(12) United States Patent
Pemberton et al.

(10) Patent No.: US 12,046,348 B2
(45) Date of Patent: Jul. 23, 2024

(54) REMOTE MONITORING AND CONTROLLING OF A PATIENT OXYGEN THERAPY DEVICE

(71) Applicant: GCE Holding AB, Malmö (SE)

(72) Inventors: Gareth Pemberton, Worcester (GB); Donald Oleforo, Malmö (SE); Chris Phillips, Malmö (SE); Mike Galvin, Malmö (SE)

(73) Assignee: GCE HOLDING AB, Malmö (SE)

( * ) Notice: Subject to any disclaimer, the term of this patent is extended or adjusted under 35 U.S.C. 154(b) by 1226 days.

(21) Appl. No.: 16/348,682

(22) PCT Filed: Nov. 11, 2016

(86) PCT No.: PCT/EP2016/077496
§ 371 (c)(1),
(2) Date: May 9, 2019

(87) PCT Pub. No.: WO2018/086710
PCT Pub. Date: May 17, 2018

(65) Prior Publication Data
US 2019/0267127 A1   Aug. 29, 2019

(51) Int. Cl.
*A61M 16/00*   (2006.01)
*G16H 20/40*   (2018.01)
*G16H 40/60*   (2018.01)

(52) U.S. Cl.
CPC .......... *G16H 20/40* (2018.01); *A61M 16/024* (2017.08); *G16H 40/60* (2018.01); *A61M 16/0051* (2013.01)

(58) Field of Classification Search
CPC ..... G16H 20/40; G16H 40/60; A61M 16/024; A61M 16/0051
See application file for complete search history.

(56) References Cited

U.S. PATENT DOCUMENTS

| | | | |
|---|---|---|---|
| 8,418,694 B2* | 4/2013 | Freitag | A61M 16/024 128/207.14 |
| 8,545,416 B1* | 10/2013 | Kayyali | A61B 5/0205 128/204.26 |
| 2005/0217671 A1* | 10/2005 | Fisher | A61M 16/204 128/205.13 |
| 2008/0251074 A1 | 10/2008 | Sand | |
| 2009/0107500 A1 | 4/2009 | Edwards | |

(Continued)

FOREIGN PATENT DOCUMENTS

| CN | 101313307 A | 11/2008 |
|---|---|---|
| CN | 103810369 A | 5/2014 |

(Continued)

OTHER PUBLICATIONS

First Examination Report for Indian Patent Application No. 201917022483 dated Dec. 6, 2021, 6 pages.

(Continued)

*Primary Examiner* — Steven O Douglas
(74) *Attorney, Agent, or Firm* — Edell, Shapiro & Finnan, LLC (57) ABSTRACT

The invention relates to a method and a user interface for remote monitoring and controlling of a patient oxygen therapy device. The invention also relates to a patient oxygen therapy device and a computer program product.

26 Claims, 5 Drawing Sheets

(56) References Cited

U.S. PATENT DOCUMENTS

| | | | |
|---|---|---|---|
| 2010/0083968 A1* | 4/2010 | Wondka | G16H 20/40 |
| | | | 128/204.23 |
| 2018/0280646 A1* | 10/2018 | Freeman | A61M 16/024 |
| 2019/0267127 A1 | 8/2019 | Pemberton et al. | |

FOREIGN PATENT DOCUMENTS

| | | | |
|---|---|---|---|
| EP | 0760247 | A2 | 3/1997 |
| EP | 3539029 | A1 | 9/2019 |
| WO | 2009055582 | A2 | 4/2009 |
| WO | 2016040954 | A2 | 3/2016 |
| WO | 2018086710 | A1 | 5/2018 |

OTHER PUBLICATIONS

International Search Report and Written Opinion for International Application No. PCT/EP2016/077496 dated Feb. 28, 2017, 11 pages.

Communication pursuant to Article 94(3) EPC for European Patent Application No. 16797830.3 dated Jun. 23, 2021, 8 pages.

First Examination Report for Chinese Patent Application No. 201680091982.7 with English translation dated Oct. 13, 2022, 14 pages.

First Examination Report for Australian Patent Application No. 2016429072 dated Oct. 6, 2022, 5 pages.

First Examination Report for Canadian Patent Application No. 3042948 dated Jan. 9, 2023, 3 pages.

Examination Report No. 2 for Australian Patent Application No. 2016429072 dated Apr. 12, 2023, 5 pages.

Second Office Action for Chinese Patent Application No. 201680091982.7 with English translation, dated Aug. 18, 2023, 12 pages.

Third Office Action for Chinese Patent Application No. 201680091982.7 with English translation, dated Dec. 20, 2023, 13 pages.

Office Action for Canadian Patent Application No. 3,042,948, dated Jan. 18, 2024, 4 pages.

\* cited by examiner

REMOTE MONITORING AND CONTROLLING OF A PATIENT OXYGEN THERAPY DEVICE

TECHNICAL FIELD

The invention relates to a method and a user interface for remote monitoring and controlling of a patient oxygen therapy device. The invention also relates to a patient oxygen therapy device and a computer program product.

BACKGROUND ART

Portable oxygen concentrators are designed to enable patients with respiratory disorders, such as chronic obstructive pulmonary disease (COPD), to better manage their oxygen therapy within and outside their homes. COPD alone afflicts hundreds of million people worldwide on a yearly basis. Supplemental oxygen therapy is also prescribed for other ailments that weaken the respiratory system, such as heart disease and AIDS, as well as for asthma and emphysema.

Portable oxygen concentrators are commercially available for providing ambulatory respiratory patients with COPD and other respiratory ailments with gaseous oxygen. A portable oxygen concentrator converts ambient air into concentrated gaseous oxygen. The portable oxygen concentrator is small and light-weight in order to allow the ambulatory respiratory patient to readily use and transport the portable oxygen concentrator inside and outside the home. As a result, the respiratory patient can lead a more active lifestyle, which in turn can improve the overall health of the patient.

US 2009/107500 A1 discloses a portable oxygen concentrator system weighing 4-20 pounds and adapted to be readily transported by a user and for delivering oxygen to lungs of the user. The system includes a rechargeable energy source, a concentrator powered by said energy source and adapted to convert ambient air into concentrated oxygen gas for said user, and a control unit that controls the concentrator to deliver a flow rate based on the current local conditions to maintain a constant fraction of inspired oxygen. The current local conditions are detailed using body temperature pressure dry, body temperature pressure saturated with water and relative humidity.

A problem with this type of portable oxygen concentrator system is the difficulty of identifying the need of maintenance of the oxygen concentrator as well as the potential need of adjustments of prescribed settings of the oxygen concentrator. This is vital since the health of the patient is dependent on a fully functioning and properly set oxygen concentrator.

SUMMARY OF THE INVENTION

It is an objective of the present invention to provide an improvement of the above technique and prior art. More particularly, it is an objective of this invention to provide an improved method of monitoring and controlling a patient oxygen therapy device.

According to a first aspect, these and other objects, and/or advantages that will be apparent from the following description of embodiments, are achieved, in full or at least in part, by a method of remote monitoring of a patient oxygen therapy device. The method comprises the steps of collecting at least one property of the patient oxygen therapy device, communicating the at least one device property to a data base, retrieving data from the data base, and displaying the data to an authorised party through a user interface.

This is advantageous in that the patient oxygen therapy device may be remotely and continuously monitored by means of the user interface. In turn, any need of maintenance of the device can easily be detected.

The at least one device property may comprise any one or all of the properties chosen from the group consisting of: location, flow rate, purity, compressor speed, humidity, barometric pressure, time of usage, date of manufacture, residual pressure, and state of back-up cylinder.

The method may further comprise the step of identifying a need of maintenance of said patient oxygen therapy device based on said at least one property. The maintenance may comprise replacement of compressor, filters and/or sieve beds.

One major problem with oxygen concentrators is knowing when to replace the sieve beds. The sieve beds, containing a Nitrogen fixing molecular sieve, are where the separation process is undertaken, typically using pressure swing absorption or vacuum swing absorption or a combination of both. The sieve beds become less efficient over time at removing Nitrogen from air due to a decreasing efficiency of molecular sieve to retain the Nitrogen. This results in the compressor running at a higher speed in order to maintain purity, and subsequently the purity is reducing until a threshold alarm level is reached. At this point in time the patient is informed that the device requires maintenance. However, it can be difficult to determine if it is the sieve beds that require replacement or if a separate fault is causing the device error. Since there are many potential reasons as to why the compressor may be running at higher speeds, for example a blocked inlet port would cause the same effect, it is important to continuously monitor the overall state of the device.

The method may further comprise the step triggering an alarm when a need of maintenance of the patient oxygen therapy device is detected. The alarm may be triggered in the user interface and/or on the patient oxygen therapy device.

According to a second aspect, these and other objects are achieved, in full or at least in part, by a method of remote control of patient oxygen therapy supply and prescription. The method comprises the steps of performing a standardised test of a patient connected to a patient oxygen therapy device while collecting at least one patient property, communicating the at least one patient property to a data base, retrieving data from the data base, displaying the data to an authorised party through a user interface, analysing the data in view of the standardised test to determine suitable prescribed settings, communicating the prescribed settings to the patient oxygen therapy device, and updating the patient oxygen therapy device based on the prescribed settings.

This is advantageous in that the state of the patient may be remotely and continuously monitored via the user interface so that the prescribed settings of the device may be updated accordingly if necessary.

The standardised test may comprise a 6-minute walk test. Patients using portable oxygen concentrators are normally suffering from a degenerative condition of their lungs. As such, the prescribed amount of Oxygen the patient requires will change over time. The prescription may be assessed by using a 6-minute walk test and the simultaneous measuring of oxygen saturation levels of the patient along with other parameters, such as distance walked and heart rate. The problem encountered by patients is that their condition may deteriorate at a rate quicker than the re-assessment periods but also they have days where their condition is worse than other days. This can lead to breathlessness of the patient and ultimately hospitalisation of the patient. In turn, this causes problems in patient care quality and cost.

The method according to the second aspect of the invention enables the oxygen concentrator to be more adaptive to patient requirements through simpler and more regular assessments using the requirements of the 6-minute walk test.

The method may further comprise the step of storing the at least one patient property in the data base as test results. Further, the step of analysing the data may comprise comparing the data with previous test results stored in the data base.

The step of analysing the data may comprise comparing the data with a usage pattern of the patient oxygen therapy device over time stored in the data base.

At least one of the steps of analysing, communicating and updating the device may be conducted remotely.

The at least one patient property may comprise any one or all of the properties chosen from the group consisting of walked distance, saturation level and heart rate. Further, the prescribed settings of the patient oxygen therapy device may comprise an output flow rate of said patient oxygen therapy device.

According to a third aspect, these and other objects are achieved, in full or at least in part, by a patient oxygen therapy device. The patient oxygen therapy device comprises an inlet air filter, means for drying the incoming air comprising at least one first flow control valve, a compressor adapted to pull in and pressurise air via the inlet air filter, sieve beds containing an absorption bed adapted to remove Nitrogen from the pressurised air, a reservoir adapted to store the final air product, means for controlling the sieve beds, the means comprising at least one second flow control valve, means for delivering the final air product to a patient, the means comprising at least one third flow control valve, and at least one patient monitoring sensor adapted to be connected to the patient, a control unit connected to the at least one patient monitoring sensor and the flow control valves, and communication means connected to the control unit and adapted to communicate with a remote data base.

The means for drying the incoming air may further comprise at least a membrane dryer.

The patient oxygen therapy device may further comprise a monitoring and transmission board, and/or a back-up memory connected to the control unit and adapted to store data in a local data base The patient oxygen therapy device may further comprise a global positioning system (GPS).

A patient oxygen therapy device is often provided for the patient by a healthcare provider. The device at some point needs to be collected from the patient and in some cases it can be difficult to find the patient oxygen therapy device due to not knowing its last location. Many healthcare providers use a team to provide asset recovery of patient oxygen therapy devices. However, they are often unable to recover the devices. This problem can be addressed by knowing the location of the device. If the patient oxygen therapy device comprises a GPS, the user interface will enable a user to actively search for the GPS location of the device. It can also be programmed to send its location on a daily basis as well as to be able to respond to requests for location information. The location of the device may also be determined using a triangulation of a radio signal from the device can be used to pinpoint its location. Further, when the device is equipped with a Wi-Fi router, the Wi-Fi connection can be used for the same purpose.

The remote data base may be accessible by a patient, a patient family, a clinician and/or a service provided through a user interface.

According to a fourth aspect, these and other objects are achieved, in full or at least in part, by a user interface for remote monitoring of a patient oxygen therapy device according to the third aspect of the invention.

According to a fifth aspect, these and other objects are achieved, in full or at least in part, by a user interface for remote control of a patient oxygen therapy device according to the third aspect of the invention. The user interface is used to control the at least one flow control valve, by means of the control unit via said communication means, based on data from the at least one patient monitoring sensor which has been stored in the remote data base.

According to a sixth aspect, these and other objects are achieved, in full or at least in part, by a computer program product. The comprises computer program product a computer-readable storage medium with instructions adapted to carry out the method according to the first or second aspect of the invention when executed by a device having processing capability.

Effects and features of the third, fourth, fifth and sixth aspect of the present invention are largely analogous to those described above in connection with the first aspect and second aspect of the inventive concept. Embodiments mentioned in relation to the first aspect of the present invention are largely compatible with the further aspects of the invention.

Other objectives, features and advantages of the present invention will appear from the following detailed disclosure, from the attached claims, as well as from the drawings. It is noted that the invention relates to all possible combinations of features.

Generally, all terms used in the claims are to be interpreted according to their ordinary meaning in the technical field, unless explicitly defined otherwise herein. All references to "a/an/the [element, device, component, means, step, etc.]" are to be interpreted openly as referring to at least one instance of said element, device, component, means, step, etc., unless explicitly stated otherwise.

As used herein, the term "comprising" and variations of that term are not intended to exclude other additives, components, integers or steps.

BRIEF DESCRIPTION OF THE DRAWINGS

The above, as well as additional objects, features and advantages of the present invention, will be better understood through the following illustrative and non-limiting detailed description of embodiments of the present invention, with reference to the appended drawings, where the same reference numerals may be used for similar elements, and wherein.

DETAILED DESCRIPTION OF PREFERRED EMBODIMENTS OF THE INVENTION

Figure 1:
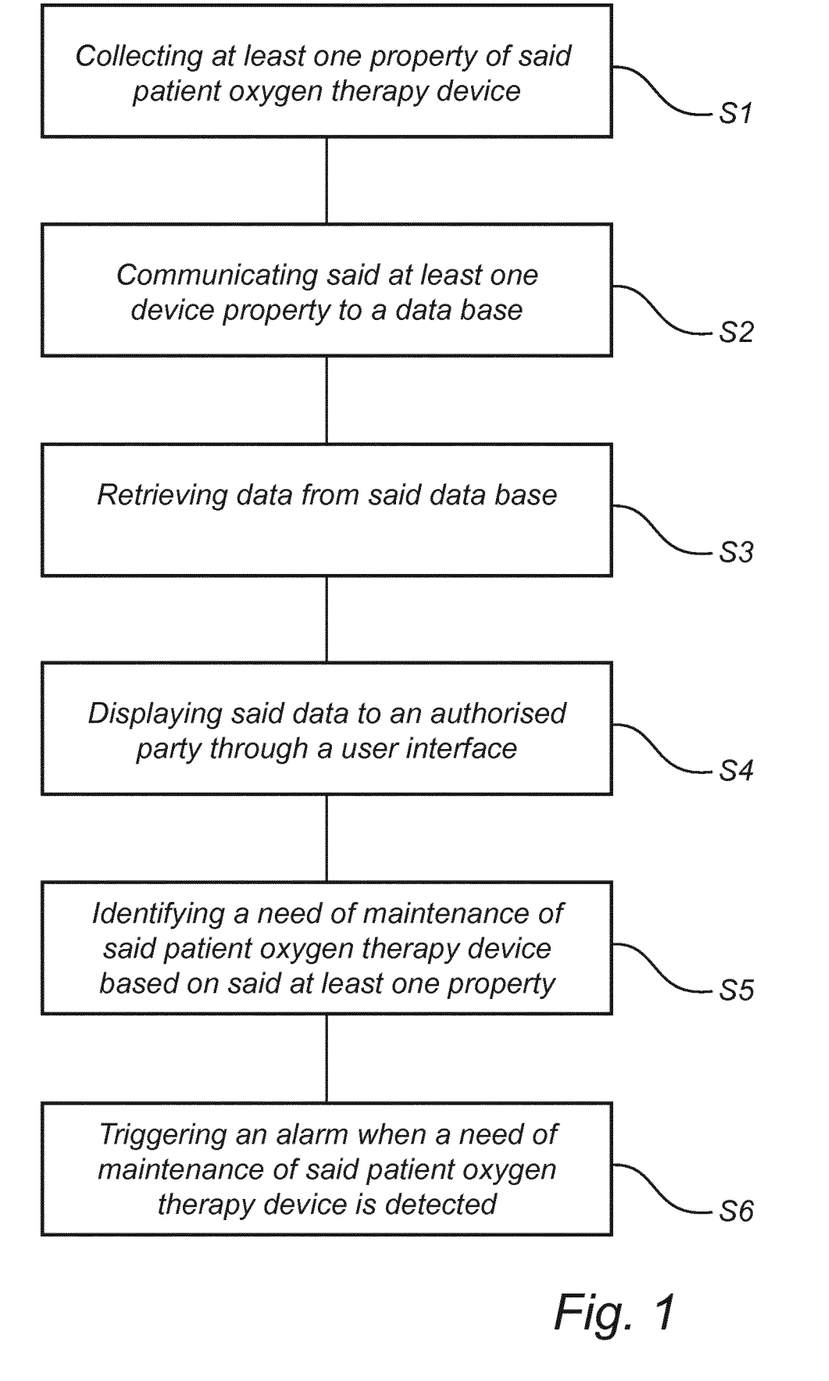
FIG. 1 is a process chart of a method of remote monitoring of a patient oxygen therapy device according to one exemplary embodiment of a first aspect of the invention.

FIG. 1 illustrates a method of remote monitoring of a patient oxygen therapy device according to one exemplary embodiment of the invention. The method comprises the steps of collecting S1 at least one property of the patient oxygen therapy device, communicating S2 the at least one device property to a data base, retrieving S3 data from the data base, displaying S4 the data to an authorised party through a user interface, identifying S5 a need of maintenance of the patient oxygen therapy device based on the at least one property, and triggering S6 an alarm when a need of maintenance of the patient oxygen therapy device is detected.

The method illustrated in FIG. 1 can also be implemented without conducting the steps of retrieving S3 data from the data base, identifying S5 a need of maintenance of the patient oxygen therapy device based on the at least one property, and triggering S6 an alarm when a need of maintenance of the patient oxygen therapy device is detected. In this case, during the step of collecting S1 at least one property of the patient oxygen therapy device, the at least one property is communicated to a user interface in real time where it can be reviewed by an authorised party.

Primarily, the maintenance of the patient oxygen therapy device includes replacement of components with different lifetimes, such as a compressor, filters and sieve beds. Since there are many potential reasons as to why the device may not function properly, it is an advantage to be able to monitor a plurality of device properties over time. Appropriate properties to monitor when determining the state of components, such as the compressor, different filters and the sieve beds, are flow rate, purity, compressor speed, humidity, barometric pressure, time of usage and date of manufacture.

It is also advantageous to store the device properties in a data base so that they can be reviewed at any time by the authorised party in order to make an assessment of the state of the device and to identify S5 whether or not there is a need for maintenance of the device.

Figure 2:
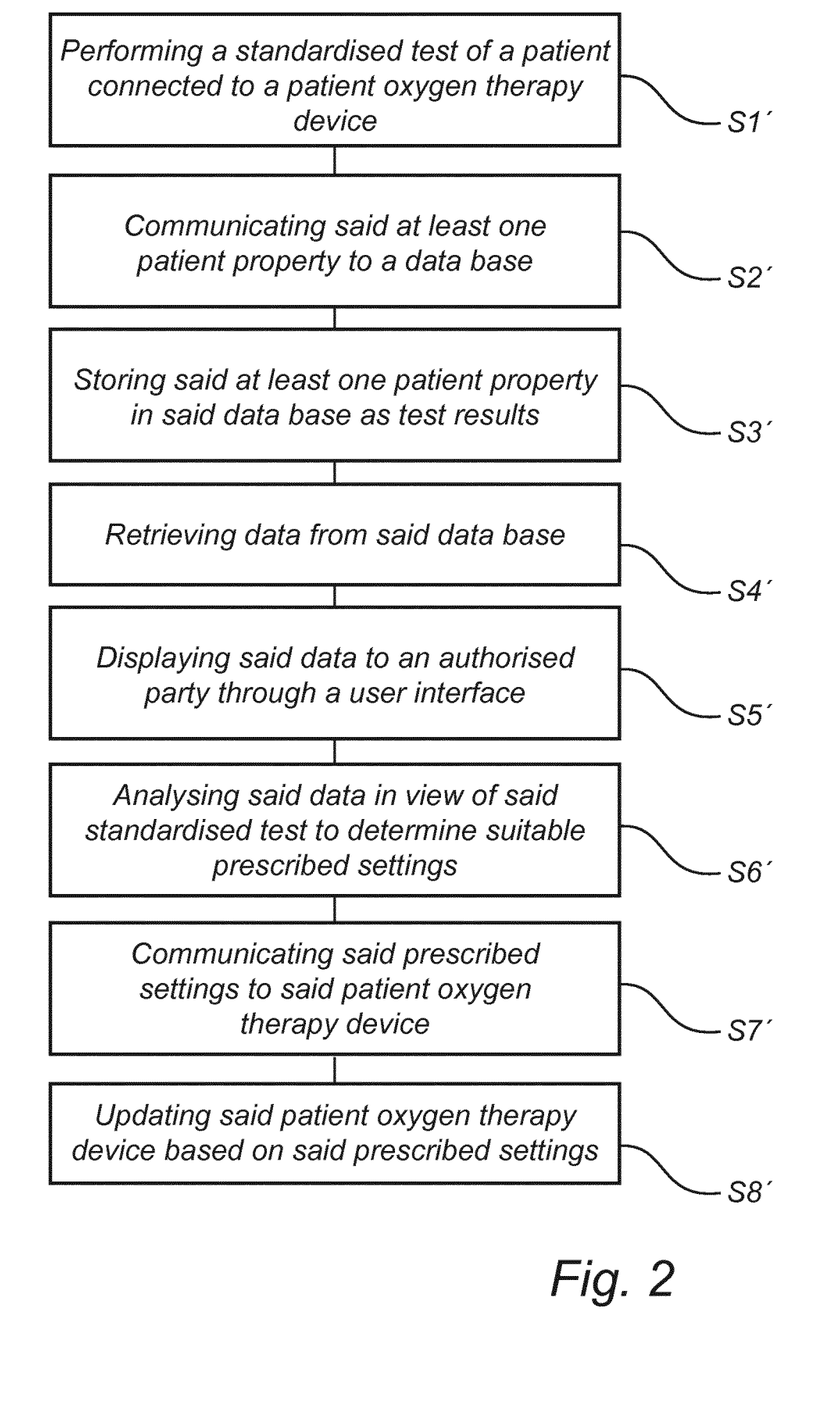
FIG. 2 is a process chart of a method of remote control of patient oxygen therapy supply and prescription according to one exemplary embodiment of a second aspect of the invention.

FIG. 2 illustrates a method of remote control of patient oxygen therapy supply and prescription according to one exemplary embodiment of the invention. The method comprises the steps of performing S1' a standardised test of a patient connected to a patient oxygen therapy device while collecting at least one patient property, communicating S2' the at least one patient property to a data base, storing S3' the at least one patient property in said data base as test results, retrieving S4' data from the data base, displaying S5' said data to an authorised party through a user interface, analysing S6' the data in view of the standardised test to determine suitable prescribed settings, communicating S7' prescribed settings to the patient oxygen therapy device, and updating S8' the patient oxygen therapy device based on the prescribed settings.

The method illustrated in FIG. 2 can also be implemented without conducting the steps of communicating S2' the at least one patient property to a data base, storing S3' the at least one patient property in said data base as test results, retrieving S4' data from the data base. In this case, during the step of performing S1' a standardised test of a patient connected to a patient oxygen therapy device while collecting at least one patient property, the at least one patient property is communicated to a user interface in real time where it can be reviewed by an authorised party. Thereafter, the steps of analysing S6' the data in view of the standardised test to determine suitable prescribed settings, communicating S7' prescribed settings to the patient oxygen therapy device, and updating S8' the patient oxygen therapy device based on the prescribed settings can be performed if appropriate.

The step of analysing S6' could include a comparison of the data with previous test results stored in said data base, or a comparison of the data with a usage pattern of the patient oxygen therapy device over time stored in said data base, in order to further improve the analysis.

Primarily, the at least one patient property comprises the walked distance during the standardised test together with the Oxygen saturation level and heart rate of the patient. By knowing these patient properties, the prescribed settings of the patient oxygen therapy device can be updated to correspond with the current health of the patient. Such a prescribed setting normally includes an output flow rate of the final air product from the patient oxygen therapy device. The prescribed setting might also state if the flow of the final air product from the patient oxygen therapy device should be continuous or in pulses.

Using this method, the state of the patient can be remotely and continuously monitored via the user interface so that the prescribed settings of the device can be updated accordingly at any appropriate time.

Naturally, the two methods described above for monitoring the patient oxygen therapy device and for remote control of patient oxygen therapy supply and prescription, respectively, are combinable in order to determine an overall state of the patient oxygen therapy device and the patient. Thereafter, appropriate action can be taken by the monitoring party.

Figure 3:
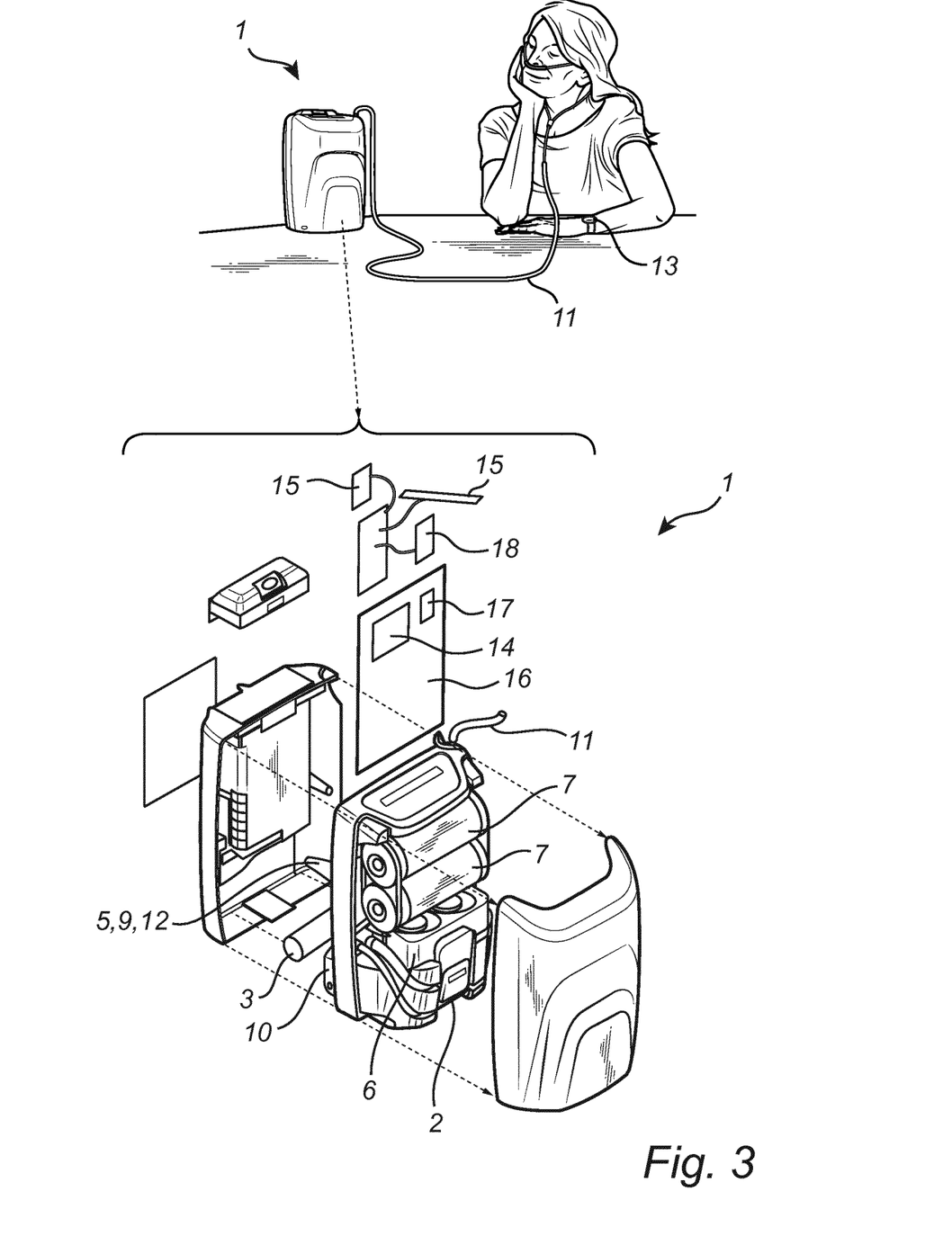
FIG. 3 is a perspective view of a patient oxygen therapy device according to one exemplary embodiment of a third aspect of the invention.

FIG. 3 illustrates a patient oxygen therapy device 1 according to one exemplary embodiment of the invention. The patient oxygen therapy device 1 comprises an inlet air filter 2 and means for drying the incoming air. The means for drying the incoming air comprises at least one membrane dryer 4 and one first flow control valve 5. The patient oxygen therapy device 1 further comprises a compressor 6 which is adapted to pull in and pressurise air via the inlet air filter 2, sieve beds 7 containing an absorption bed (not shown) adapted to remove Nitrogen from said pressurised air, and means for controlling the sieve beds 7. The means for controlling the sieve beds 7 comprises at least one second flow control valve 9. The patient oxygen therapy device 1 further comprises a reservoir 10 which is adapted to store the final air product and means 11 for delivering the final air product to a patient. The means 11 for delivering the final air product to the patient comprises at least one third flow control valve 12. The patient oxygen therapy device 1 further comprises at least one patient monitoring sensor 13 adapted to be connected to the patient (a wireless connection is possible), a control unit 14 connected to the at least one patient monitoring sensor 13 and the flow control valves 5, 9, 12, and communication means or module 15 connected to the control unit 14 and adapted to communicate with a remote data base. The remote data base is then remotely accessible by a patient, a patient family, a clinician and/or a service provided through a user interface. The communication means or module 15 could for example be constituted by a near field communication (NFC) antenna and/or a global system for mobile communication (GSM) antenna.

In a preferred embodiment, the patient oxygen therapy device 1 further comprises a monitoring and transmission board 16, a back-up memory 17 connected to the control unit 14 and adapted to store data in a local data base, and a global positioning system (GPS) 18. When the patient oxygen therapy device 1 comprises a GPS 18, the user interface will enable a user to actively search for the GPS location of the device 1. As an alternative, a triangulation of a radio signal from the device 1 can be used to pinpoint its location. Also, where the device 1 is equipped with a Wi-Fi router, the Wi-Fi connection can be used for the same purpose.

In another preferred embodiment, the patient oxygen therapy device 1 further comprises a back-up oxygen cylinder (not shown) in case of a power failure or concentrator malfunction. Currently, healthcare providers have difficulties to remotely monitor the back-up oxygen cylinder, in view of content and use, and must therefore rely on the patient to provide such information or on visits to the patient. With the present invention such information can be retrieved from the patient oxygen therapy device 1 by using the methods described above. The information is retrieved via Bluetooth or via another wireless protocol NFC. Thereafter, the information is used to predict replenishment requirements and optimize maintenance of the device 1.

The back-up oxygen cylinder includes a residual pressure valve (not shown). By monitoring the residual pressure valve, it is possible to identify the state of the back-up oxygen cylinder for collection. The identification of the functionality of the residual pressure valve is currently only possible by the gas filling company by using some form of hand tool. The problem this causes is that the back-up oxygen cylinder is required to be purged and vacuumed before re-filling and the service provider may not take advantage of legislation to increase the inspection and test of the cylinder to 15 years from 10 years.

Figure 4:
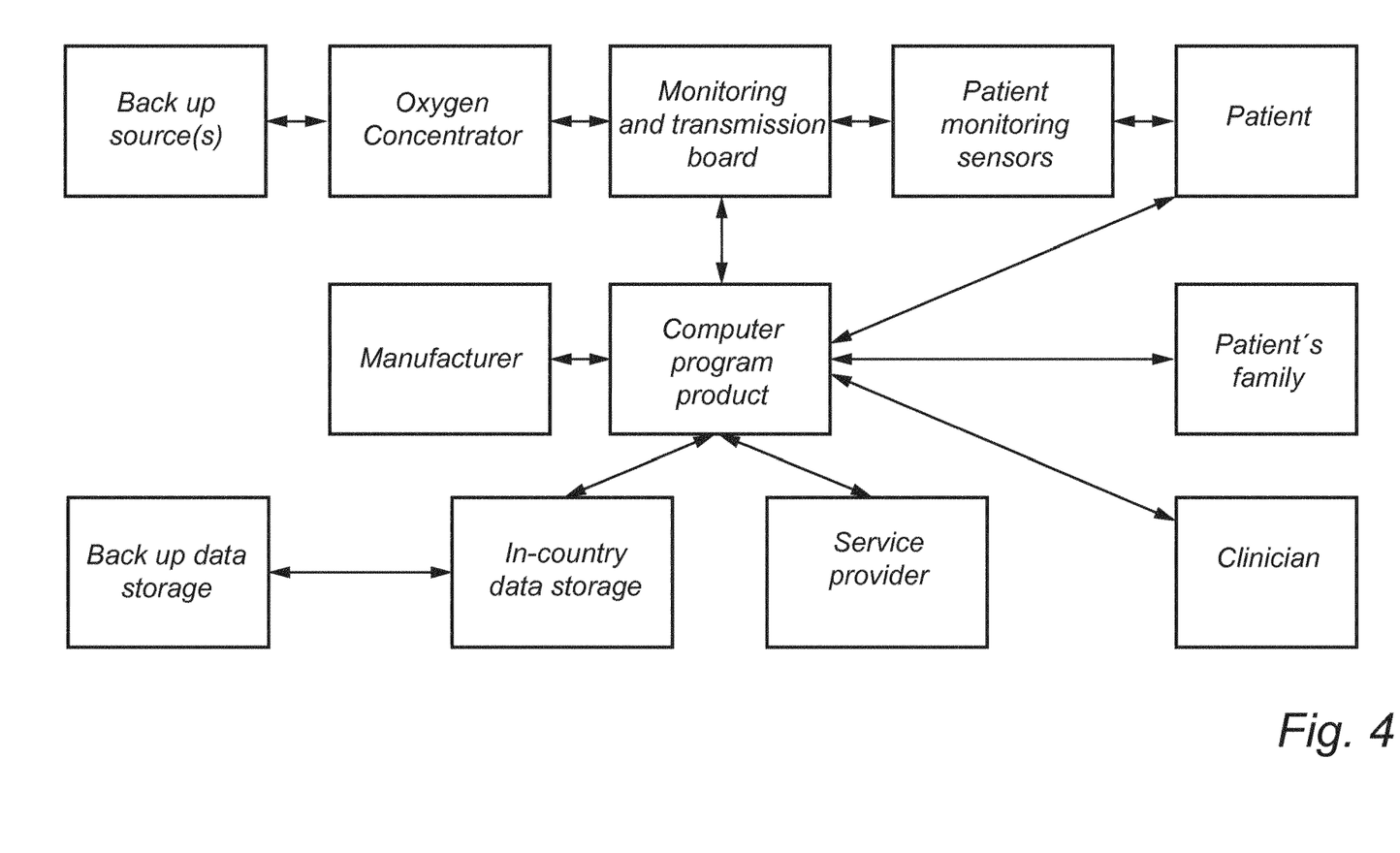
FIG. 4 is a general overview of the interconnection between different aspects of the invention.
Figure 5:
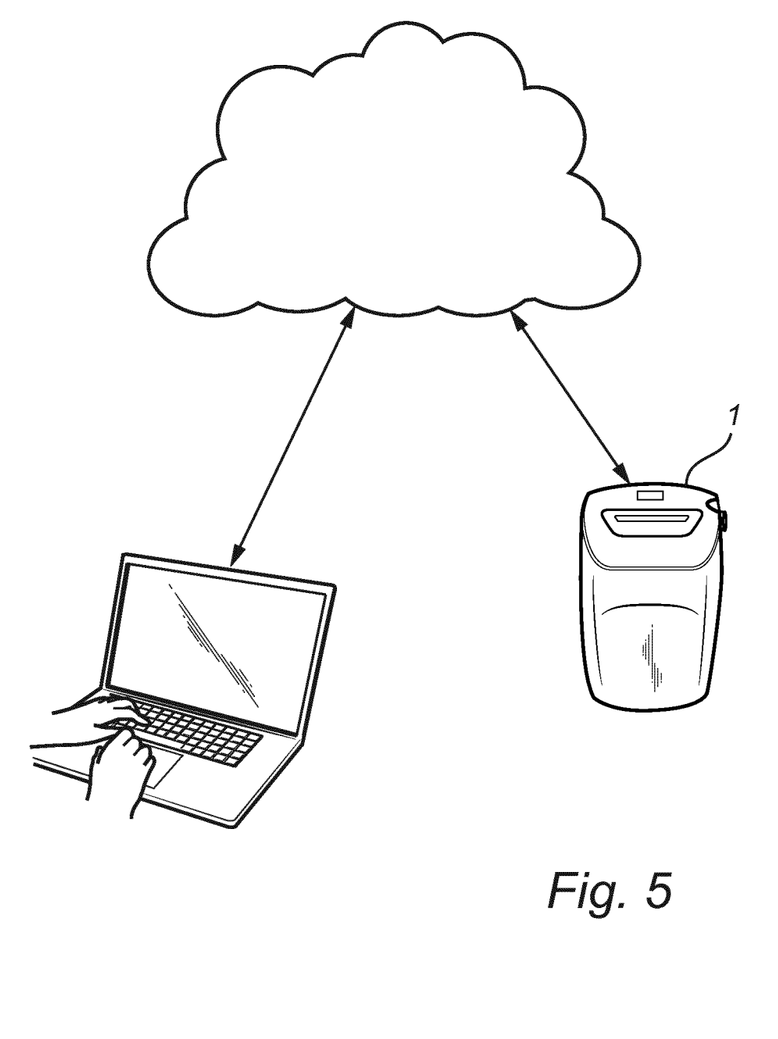
FIG. 5 is a perspective view of a system for remote monitoring and controlling of a patient oxygen therapy device through a wireless connection.

In FIG. 4, a general overview of the interconnection between different aspects of the invention is illustrated. By using a computer program product which comprises a computer-readable storage medium with instructions adapted to carry out the method(s) described above, when executed by a device having processing capability, the objectives of the present invention can be achieved. Basically, by means of a computer or a smart phone (FIG. 5), the patient oxygen therapy device 1 as well as the health state of the patient can be remotely monitored and controlled through the user interface.

The skilled person realizes that a number of modifications of the embodiments described herein are possible without departing from the scope of the invention, which is defined in the appended claims.

For instance, the monitoring and transmission board may be equipped with a NFC antenna. It is to be used for NFC identification of a valid sieve bed and compressor and also to identify if the maintenance is authorised and completed correctly.

The invention claimed is:

1. A method of monitoring a patient oxygen therapy device that comprises an inlet air filter, at least one first flow control valve for drying incoming air, a compressor adapted to pull in and pressurize air via the inlet air filter, sieve beds containing an absorption bed adapted to remove Nitrogen from the pressurised air, at least one second flow control valve for controlling the sieve beds, a reservoir adapted to store a final air product, and at least one third flow control valve for delivering the final air product to a patient, the method comprising:
monitoring at least one device property of said patient oxygen therapy device;
determining a status of a component of said patient oxygen therapy device based on the at least one device property;
transmitting, via a communication module, a maintenance signal to an authorised party in response to the determined status of the component; and
receiving a signal from a remote device to control the component.

2. The method according to claim 1, wherein at least one device property comprises at least one of location, flow rate, purity, compressor speed, humidity, barometric pressure, time of usage, date of manufacture, residual pressure, and state of back-up cylinder.

3. The method according to claim 1, wherein determining the status of the component comprises:
identifying a need of maintenance of said patient oxygen therapy device when said at least one device property does not meet a criteria.

4. The method according to claim 3, wherein said maintenance comprises replacement of a compressor, filters, and/or sieve beds.

5. The method according to claim 3, further comprising: triggering an alarm when a need of maintenance of said patient oxygen therapy device is detected.

6. The method according to claim 5, wherein said alarm is triggered at said patient oxygen therapy device.

7. The method of claim 1, further comprising:
performing standardised test of a patient connected to said patient oxygen therapy device while monitoring at least one patient property;
obtaining suitable prescribed settings based on said standardised test and additional data retrieved from a data base; and
updating said patient oxygen therapy device based on said prescribed settings.

8. The method according to claim 7, wherein said standardised test comprises a 6-minute walk test.

9. The method according to claim 7, further comprising: transmitting said at least one patient property to said data base for storage as test results.

10. The method according to claim 9, further comprising: analysing said additional data with previous test results collected from said data base.

11. The method according to claim 10, wherein the analysing of said additional data comprises comparing said additional data with a usage pattern of said patient oxygen therapy device over time collected from said data base.

12. The method according to claim 9, wherein at least one of an analysis and an update is received by said patient oxygen therapy device remotely.

13. The method according to claim 7, wherein said at least one patient property comprises at least one of: walked distance, saturation level and heart rate.

14. The method according to claim 7, wherein said prescribed settings comprise an output flow rate of said patient oxygen therapy device.

15. The method of claim 1, wherein said patient oxygen therapy device comprises:
at least one patient monitoring sensor adapted to be connected to said patient; and
a control unit connected to said at least one patient monitoring sensor and said at least one first flow control valve, said at least one second flow control valve, and said at least one third flow control valve;
wherein said communication module is connected to said control unit and adapted to communicate with a remote data base.

16. The method of claim 15, wherein said patient oxygen therapy device further comprises a monitoring and transmission board.

17. The method of claim 15, wherein said patient oxygen therapy device further comprises a back-up memory connected to said control unit and adapted to store data in a local data base.

18. The method of claim 15, wherein said patient oxygen therapy device further comprises a global positioning system (GPS).

19. The method of claim 15, further comprising receiving, at said control unit, control signals for said at least one first flow control valve, said at least one second flow control valve, and said at least one third flow control valve based on data from said at least one patient monitoring sensor, the data obtained from said remote data base.

20. A computer program product, comprising a computer-readable storage medium with instructions adapted to carry out the method of claim 1 when executed by a device having processing capability.

21. A computer program product, comprising a computer-readable storage medium with instructions adapted to carry out the method of claim 7 when executed by a device having processing capability.

22. The method of claim 1, wherein said transmitting said maintenance signal to said authorised party occurs in real time.

23. The method according to claim 3, wherein identifying a need of maintenance of said patient oxygen therapy device occurs remotely.

24. The method according to claim 1, wherein receiving a signal from a remote device to control the component includes receiving the signal via the communication module.

25. The method according to claim 1, wherein the at least one device property is a state of a back-up cylinder, and the monitoring at least one device property includes monitoring a valve of the back-up cylinder.

26. The method according to claim 1, wherein monitoring and controlling of the patient oxygen therapy device occurs through a wireless connection and a user interface.

* * * * *